(12) United States Patent
Volpe et al.

(10) Patent No.: US 8,897,860 B2
(45) Date of Patent: *Nov. 25, 2014

(54) SELECTION OF OPTIMAL CHANNEL FOR RATE DETERMINATION

(75) Inventors: Shane S. Volpe, Saltsburg, PA (US); Thomas E. Kaib, North Huntingdon, PA (US)

(73) Assignee: Zoll Medical Corporation, Chelmsford, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/428,329

(22) Filed: Mar. 23, 2012

(65) Prior Publication Data

US 2012/0302860 A1    Nov. 29, 2012

Related U.S. Application Data

(60) Provisional application No. 61/467,599, filed on Mar. 25, 2011.

(51) Int. Cl.
| | | |
|---|---|---|
| A61B 5/0408 | (2006.01) | |
| A61B 5/0432 | (2006.01) | |
| A61B 5/0452 | (2006.01) | |
| A61N 1/39 | (2006.01) | |
| A61N 1/04 | (2006.01) | |
| A61B 5/00 | (2006.01) | |

(52) U.S. Cl.
CPC .......... *A61N 1/3925* (2013.01); *A61B 5/04525* (2013.01); *A61N 1/0484* (2013.01); *A61N 1/046* (2013.01); *A61B 5/6805* (2013.01); *A61B 5/04085* (2013.01); *A61B 5/7221* (2013.01); *A61B 2560/0266* (2013.01); *A61B 5/0006* (2013.01); *A61N 1/0476* (2013.01)
USPC ............ 600/509; 600/388; 600/391; 600/512

(58) Field of Classification Search
USPC .................................... 600/483, 509
See application file for complete search history.

(56) References Cited

U.S. PATENT DOCUMENTS

| | | | |
|---|---|---|---|
| 4,094,310 A | 6/1978 | McEachern et al. | |
| 4,632,122 A | 12/1986 | Johansson et al. | |

(Continued)

FOREIGN PATENT DOCUMENTS

| | | |
|---|---|---|
| DE | 2644236 C3 | 4/1981 |
| EP | 0295497 B1 | 9/1993 |

(Continued)

OTHER PUBLICATIONS

American Journal of Respiratory and Critical Care Medicine, vol. 166, pp. 111-117 (2002), American Thoracic Society, ATS Statement: Guidelines for the Six-Minute Walk Test, available at http://ajrccm.atsjournals.org/cgi/content/full/166/1/111.

(Continued)

*Primary Examiner* — Carl H Layno
*Assistant Examiner* — Erin Piateski
(74) *Attorney, Agent, or Firm* — Lando & Anastasi, LLP

(57) ABSTRACT

According to at least one example, an ambulatory medical device is provided. The device includes a plurality of electrodes disposed at spaced apart positions about a patient's body and a control unit. The control unit includes a sensor interface, a memory and a processor. The sensor interface is coupled to the plurality of electrodes and configured to receive a first ECG signal from a first pairing of the plurality of electrodes and to receive a second ECG signal from a second pairing of the plurality of electrodes. The memory stores information indicating a preferred pairing, the preferred pairing being either the first pairing or the second pairing. The processor is coupled to the sensor interface and the memory and is configured to resolve conflicts between interpretations of first ECG signal and the second ECG signal in favor of the preferred pairing.

23 Claims, 6 Drawing Sheets

(56) References Cited

U.S. PATENT DOCUMENTS

| | | |
|---|---|---|
| 4,928,690 A | 5/1990 | Heilman et al. |
| 4,978,926 A | 12/1990 | Zerod et al. |
| 4,991,217 A | 2/1991 | Garrett et al. |
| 5,062,834 A | 11/1991 | Gross et al. |
| 5,078,134 A | 1/1992 | Heilman et al. |
| 5,348,008 A | 9/1994 | Bornn et al. |
| 5,365,932 A | 11/1994 | Greenhut |
| 5,381,798 A | 1/1995 | Burrows |
| 5,472,453 A | 12/1995 | Alt |
| 5,662,689 A | 9/1997 | Elsberry et al. |
| 5,718,242 A | 2/1998 | McClure et al. |
| 5,738,102 A | 4/1998 | Lemelson |
| 5,741,306 A | 4/1998 | Glegyak et al. |
| 5,758,443 A | 6/1998 | Pedrazzini |
| 5,792,190 A | 8/1998 | Olson et al. |
| 5,827,196 A | 10/1998 | Yeo et al. |
| 5,887,978 A | 3/1999 | Lunghofer et al. |
| 5,929,601 A | 7/1999 | Kaib et al. |
| 5,944,669 A | 8/1999 | Kaib |
| 6,016,445 A | 1/2000 | Baura |
| 6,045,503 A | 4/2000 | Grabner et al. |
| 6,047,203 A | 4/2000 | Sackner et al. |
| 6,065,154 A | 5/2000 | Hulings et al. |
| 6,097,982 A | 8/2000 | Glegyak et al. |
| 6,097,987 A | 8/2000 | Milani |
| 6,148,233 A | 11/2000 | Owen et al. |
| 6,169,397 B1 | 1/2001 | Steinbach et al. |
| 6,253,099 B1 | 6/2001 | Oskin et al. |
| 6,280,461 B1 | 8/2001 | Glegyak et al. |
| 6,390,996 B1 | 5/2002 | Halperin et al. |
| 6,406,426 B1 | 6/2002 | Reuss et al. |
| 6,681,003 B2 | 1/2004 | Linder et al. |
| 6,690,969 B2 | 2/2004 | Bystrom et al. |
| 6,804,554 B2 | 10/2004 | Ujhelyi et al. |
| 6,827,695 B2 | 12/2004 | Palazzolo et al. |
| 6,908,437 B2 | 6/2005 | Bardy |
| 6,925,330 B2 * | 8/2005 | Kleine ................. 607/9 |
| 6,961,612 B2 | 11/2005 | Elghazzawi et al. |
| 6,990,373 B2 | 1/2006 | Jayne et al. |
| 7,149,579 B1 | 12/2006 | Koh et al. |
| 7,220,235 B2 | 5/2007 | Geheb et al. |
| 7,340,296 B2 | 3/2008 | Stahmann et al. |
| 7,453,354 B2 | 11/2008 | Reiter et al. |
| 7,488,293 B2 | 2/2009 | Marcovecchio et al. |
| 7,712,373 B2 | 5/2010 | Nagle et al. |
| 7,831,303 B2 | 11/2010 | Rueter et al. |
| 7,974,689 B2 | 7/2011 | Volpe et al. |
| 7,991,460 B2 | 8/2011 | Fischell et al. |
| 8,121,683 B2 | 2/2012 | Bucher et al. |
| 8,140,154 B2 | 3/2012 | Donnelly et al. |
| 8,271,082 B2 | 9/2012 | Donnelly et al. |
| 2003/0004547 A1 | 1/2003 | Owen et al. |
| 2003/0095648 A1 | 5/2003 | Kaib et al. |
| 2003/0109904 A1 | 6/2003 | Silver et al. |
| 2003/0149462 A1 | 8/2003 | White et al. |
| 2003/0158593 A1 | 8/2003 | Heilman et al. |
| 2003/0174049 A1 | 9/2003 | Beigel et al. |
| 2003/0195567 A1 | 10/2003 | Jayne et al. |
| 2003/0212311 A1 | 11/2003 | Nova et al. |
| 2004/0010294 A1 * | 1/2004 | Kleine ................. 607/18 |
| 2004/0049233 A1 | 3/2004 | Edwards |
| 2004/0162510 A1 | 8/2004 | Jayne et al. |
| 2004/0249419 A1 | 12/2004 | Chapman et al. |
| 2005/0049515 A1 | 3/2005 | Misczynski et al. |
| 2005/0131465 A1 | 6/2005 | Freeman et al. |
| 2005/0246199 A1 | 11/2005 | Futch |
| 2005/0283198 A1 | 12/2005 | Haubrich et al. |
| 2006/0036292 A1 | 2/2006 | Smith et al. |
| 2006/0085049 A1 | 4/2006 | Cory et al. |
| 2006/0178706 A1 | 8/2006 | Lisogurski et al. |
| 2006/0211934 A1 | 9/2006 | Hassonjee et al. |
| 2006/0270952 A1 | 11/2006 | Freeman et al. |
| 2007/0118056 A1 | 5/2007 | Wang et al. |
| 2007/0143864 A1 | 6/2007 | Cabana et al. |
| 2007/0161913 A1 | 7/2007 | Farrell et al. |
| 2007/0169364 A1 | 7/2007 | Townsend et al. |
| 2007/0197878 A1 | 8/2007 | Shklarski |
| 2007/0239214 A1 | 10/2007 | Cinbis |
| 2007/0239220 A1 * | 10/2007 | Greenhut et al. ................. 607/32 |
| 2007/0265671 A1 | 11/2007 | Roberts et al. |
| 2008/0004536 A1 | 1/2008 | Baxi et al. |
| 2008/0021532 A1 | 1/2008 | Kveen et al. |
| 2008/0030656 A1 | 2/2008 | Watson et al. |
| 2008/0033495 A1 | 2/2008 | Kumar |
| 2008/0045815 A1 | 2/2008 | Derchak et al. |
| 2008/0046015 A1 | 2/2008 | Freeman et al. |
| 2008/0058884 A1 | 3/2008 | Matos |
| 2008/0103402 A1 | 5/2008 | Stickney et al. |
| 2008/0167535 A1 | 7/2008 | Stivoric et al. |
| 2008/0177341 A1 | 7/2008 | Bowers |
| 2008/0183090 A1 * | 7/2008 | Farringdon et al. ........... 600/509 |
| 2008/0249591 A1 | 10/2008 | Gaw et al. |
| 2008/0287749 A1 | 11/2008 | Reuter |
| 2008/0294019 A1 | 11/2008 | Tran |
| 2008/0306560 A1 * | 12/2008 | Macho et al. .................. 607/5 |
| 2008/0312520 A1 | 12/2008 | Rowlandson et al. |
| 2008/0312522 A1 | 12/2008 | Rowlandson et al. |
| 2008/0312709 A1 | 12/2008 | Volpe et al. |
| 2009/0018428 A1 | 1/2009 | Dias et al. |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0093687 A1 | 4/2009 | Telfort et al. |
| 2009/0138059 A1 | 5/2009 | Ouwerkerk |
| 2009/0146822 A1 | 6/2009 | Soliman |
| 2009/0234410 A1 | 9/2009 | Libbus et al. |
| 2009/0264792 A1 | 10/2009 | Mazar |
| 2009/0275848 A1 | 11/2009 | Brockway et al. |
| 2009/0281394 A1 | 11/2009 | Russell et al. |
| 2009/0287120 A1 | 11/2009 | Ferren et al. |
| 2009/0292194 A1 | 11/2009 | Libbus et al. |
| 2009/0295326 A1 | 12/2009 | Daynes et al. |
| 2009/0307266 A1 | 12/2009 | Fleizach et al. |
| 2009/0318779 A1 | 12/2009 | Tran |
| 2010/0052892 A1 | 3/2010 | Allen et al. |
| 2010/0052897 A1 | 3/2010 | Allen et al. |
| 2010/0056881 A1 | 3/2010 | Libbus et al. |
| 2010/0069735 A1 | 3/2010 | Berkner |
| 2010/0076513 A1 * | 3/2010 | Warren et al. .................. 607/17 |
| 2010/0081962 A1 | 4/2010 | Hamaguchi et al. |
| 2010/0114243 A1 | 5/2010 | Nowak et al. |
| 2010/0234716 A1 | 9/2010 | Engel |
| 2010/0241181 A1 | 9/2010 | Savage et al. |
| 2010/0295674 A1 | 11/2010 | Hsieh et al. |
| 2010/0298899 A1 | 11/2010 | Donnelly et al. |
| 2011/0015533 A1 | 1/2011 | Cox et al. |
| 2011/0093840 A1 | 4/2011 | Pynenburg et al. |
| 2011/0098765 A1 | 4/2011 | Patel |
| 2011/0288604 A1 | 11/2011 | Kaib et al. |
| 2011/0288605 A1 * | 11/2011 | Kaib et al. ..................... 607/5 |
| 2012/0011382 A1 | 1/2012 | Volpe et al. |
| 2012/0053479 A1 | 3/2012 | Hopenfeld |
| 2012/0112903 A1 | 5/2012 | Kaib et al. |
| 2012/0146797 A1 | 6/2012 | Oskin et al. |
| 2012/0150008 A1 | 6/2012 | Kaib et al. |
| 2012/0158075 A1 | 6/2012 | Kaib et al. |

(56) References Cited

U.S. PATENT DOCUMENTS

FOREIGN PATENT DOCUMENTS

| | | | |
|---|---|---|---|
| EP | 0335356 B1 | 3/1996 |
| EP | 1455640 B1 | 1/2008 |
| EP | 1720446 B1 | 7/2010 |
| JP | 5115450 A | 5/1993 |
| JP | 2002200059 A | 7/2002 |
| WO | 0002484 A1 | 1/2000 |
| WO | 2004054656 A1 | 7/2004 |
| WO | 2004067083 A2 | 8/2004 |
| WO | 2004078259 A1 | 9/2004 |
| WO | 2005082454 A1 | 9/2005 |
| WO | 2006050325 A2 | 5/2006 |
| WO | 2007019325 A2 | 2/2007 |
| WO | 2009034506 A1 | 3/2009 |
| WO | 2010025432 A1 | 3/2010 |
| WO | 2010077997 A2 | 7/2010 |

OTHER PUBLICATIONS

DeBock, et al., "Captopril treatment of chronic heart failure in the very old," J. Gerontol. (1994) 49: M148-M152.

O'Keeffe et al., "Reproducability and responsiveness of quality of life assessment and six minute walk test in elderly heart failure patients," Heart (1998) 80: 377-382.

http://web.archive.org/web/20030427001846/http:/www.lifecor.com/imagelib/imageproduct.asp. Published by LifeCor, Inc., 2002, on a webpage owned by LifeCor, Inc.

* cited by examiner

SELECTION OF OPTIMAL CHANNEL FOR RATE DETERMINATION

RELATED APPLICATIONS

This application claims priority under 35 U.S.C. §119(e) to U.S. Provisional Application Ser. No. 61/467,599, entitled "SELECTION OF OPTIMAL CHANNEL FOR RATE DETERMINATION," filed on Mar. 25, 2011, which is hereby incorporated herein by reference in its entirety.

BACKGROUND

1. Technical Field

Examples disclosed herein relate generally to the detection of cardiac function in a patient, and more particularly to the detection of cardiac function and the treatment of cardiac conditions in an ambulatory medical device, such as a wearable defibrillator.

2. Discussion

With a wearable defibrillator worn by an ambulatory patient, the patient's electrocardiogram (ECG) signal is obtained from body surface electrodes. Determining the true characteristics of an ambulatory patient's cardiac cycle based on an ECG signal in this manner can be difficult. Electrical noise and electrode fall-off frequently degrade the quality of the ECG signal. In addition, the characteristics of ECG signals vary from patient to patient due to factors such as the patient's state of health, individual physiology, and electrode positions on the body surface.

Known ambulatory wearable defibrillators, such as the LifeVest® Wearable Cardioverter Defibrillator available from Zoll Medical Corporation of Chelmsford, Mass., use four ECG sensing electrodes in a dual-channel configuration. That is, an electrical signal provided by one of the four ECG sensing electrodes is paired with the electrical signal provided by another of the four ECG sensing electrodes to form a channel. This arrangement of ECG sensing electrodes is usually suitable because in most cases it is rare that noise or electrode movement affects the entire body circumference. The dual-channel configuration provides redundancy and allows the system to operate on a single channel if necessary. Because signal quality also varies from patient to patient, having two channels provides the opportunity to have improved signal pickup, since the ECG sensing electrodes are located in different body positions.

SUMMARY

Examples disclosed herein are directed to a wearable medical device that monitors ECG signals received on a plurality of channels and interprets the ECG signals according to a set of preferences. This set of preferences indicates which to channels and detection methods are more likely to provide accurate results for the patient wearing the wearable medical device. By interpreting ECG signals according to the set of preferences, the wearable medical device decreases the frequency of falsely detected cardiac malfunctions.

According to one example, an ambulatory medical device is provided. The device includes a plurality of electrodes disposed at spaced apart positions about a patient's body and a control unit. The control unit includes a sensor interface coupled to the plurality of electrodes and configured to receive a first ECG signal from a first pairing of the plurality of electrodes and to receive a second ECG signal from a second pairing of the plurality of electrodes, a memory storing information indicating a preferred pairing, the preferred pairing being either the first pairing or the second pairing and a processor coupled to the sensor interface and the memory and configured to resolve conflicts between interpretations of first ECG signal and the second ECG signal in favor of the preferred pairing. In some examples, the first pairing includes electrodes that are distinct from the electrodes included in the second pairing. In other examples, one of the plurality of electrodes is common between the first and second pairings. The device may include a plurality of electrodes that are integrated into a garment that is worn about a patient's body. In addition, the interpretations of the ECG signals may detect heartbeats.

According to another example, a method of monitoring ECG signals is provided. In some examples, the method is executed by an ambulatory medical device as described herein. The method includes acts of determining a first interpretation of a first ECG signal provided by a first channel of the plurality of channels, determining a second interpretation of a second ECG signal provided by a second channel of the plurality of channels, determining which one of the first channel and the second channel provides a more reliable ECG signal and resolving a conflict between the first interpretation and the second interpretation based upon which of the first channel and the second channel is determined to provide the more reliable ECG signal.

According to at least one example, an ambulatory medical device is provided. The device includes a plurality of electrodes disposed at spaced apart positions about to a patient's body and a control unit. The control unit includes a sensor interface, a memory and a processor. The sensor interface is coupled to the plurality of electrodes and configured to receive a first ECG signal from a first pairing of the plurality of electrodes and to receive a second ECG signal from a second pairing of the plurality of electrodes. The memory stores information indicating a preferred pairing, the preferred pairing being either the first pairing or the second pairing. The processor is coupled to the sensor interface and the memory and is configured to resolve conflicts between interpretations of first ECG signal and the second ECG signal in favor of the preferred pairing.

The device may further comprise a garment that is configured to be worn about the patient's body. The plurality of electrodes may be integrated into the garment. The plurality of electrodes may include adhesive electrodes. In some examples, the interpretations of the ECG signals may detect heartbeats.

In the device, the information indicating the preferred pairing may include information indicating a first heart rate detection method preferred for the first pairing and a second heart rate detection method preferred for the second pairing. The processor may be further configured to interpret the first ECG signal using the first heart rate detection method and interpret the second ECG signal using the second heart rate detection method.

In the device, the processor may be further configured to determine a first confidence level for the first pairing, determine a second confidence level for the second pairing, determine the preferred pairing with reference to the first confidence level and the second confidence level and store the information indicating the preferred pairing in the memory. In addition, the processor may be configured to determine the first confidence level by comparing the first ECG signal to benchmark information. The benchmark information may reflect a particular patient's normal rhythm. In addition, the processor may be configured to compare the first ECG signal to the benchmark information by comparing a morphology of the first ECG signal to a morphology indicated within the benchmark information.

According to another example, a method of monitoring ECG signals using an ambulatory medical device is provided. The method includes acts of receiving, by the to ambulatory medical device, a first ECG signal from a first pairing of a plurality of electrodes, receiving a second ECG signal from a second pairing of the plurality of electrodes and resolving conflicts between interpretations of first ECG signal and the second ECG signal in favor of a preferred pairing being either the first paring or the second pairing.

In the method, the act of resolving the conflicts between the interpretations may include resolving conflicts between interpretations that detect heartbeats. The method may further comprise acts of interpreting the first ECG signal using a first heart rate detection method and interpreting the second ECG signal using a second heart rate detection method. The first heart rate detection method may be different from the second heart rate detection method.

The method may further comprise acts of determining a first confidence level for the first pairing, determining a second confidence level for the second pairing and determining the preferred pairing with reference to the first confidence level and the second confidence level. In the method, the act of determining the first confidence level may include an act of comparing the first ECG signal to benchmark information. The act of comparing the first ECG signal to the benchmark information may include comparing the first ECG signal to benchmark information that reflects a particular patient's normal rhythm. In addition, the act of comparing the first ECG signal to the benchmark information may include comparing a morphology of the first ECG signal to a morphology indicated within the benchmark information.

In another example, a non-transitory computer readable medium having stored thereon sequences of instruction for monitoring ECG signals is provided. The instructions instruct at least one processor to receive a first ECG signal from a first pairing of the plurality of electrodes, receive a second ECG signal from a second pairing of the plurality of electrodes and resolve conflicts between interpretations of first ECG signal and the second ECG signal in favor of a preferred pairing being either the first pairing or the second pairing.

Furthermore, the instructions may further instruct the at least one processor to determine a first confidence level for the first pairing, determine a second confidence to level for the second pairing and determine the preferred pairing with reference to the first confidence level and the second confidence level. The instructions that instruct the at least one processor to determine the first confidence level may include instructions that instruct the at least one processor to compare the first ECG signal to benchmark information. The instructions that instruct the at least one processor to compare the first ECG signal to the benchmark information may include instructions that instruct the at least one processor to compare a morphology of the first ECG signal to a morphology indicated within the benchmark information.

Still other aspects, examples, and advantages of these exemplary aspects and examples, are discussed in detail below. Moreover, it is to be understood that both the foregoing information and the following detailed description are merely illustrative examples of various aspects, and are intended to provide an overview or framework for understanding the nature and character of the claimed subject matter. References to "an example," "some examples," "an alternate example," "various examples," "one example," "at least one example," "this and other examples" or the like are not necessarily mutually exclusive and are intended to indicate that a particular feature, structure, or characteristic described in connection with the example may be included in that example and other examples. The appearances of such terms herein are not necessarily all referring to the same example.

Furthermore, in the event of inconsistent usages of terms between this document and documents incorporate herein by reference, the term usage in the incorporated references is supplementary to that of this document; for irreconcilable inconsistencies, the term usage in this document controls. In addition, the accompanying drawings are included to provide illustration and a further understanding of the various aspects and examples, and are incorporated in and constitute a part of this specification. The drawings, together with the remainder of the specification, serve to explain principles and operations of the described and claimed aspects and examples.

BRIEF DESCRIPTION OF DRAWINGS

The accompanying drawings are not intended to be drawn to scale. In the to drawings, components that are identical or nearly identical may be represented by a like numeral. For purposes of clarity, not every component is labeled in every drawing. In the drawings.

DETAILED DESCRIPTION

Figure 1:
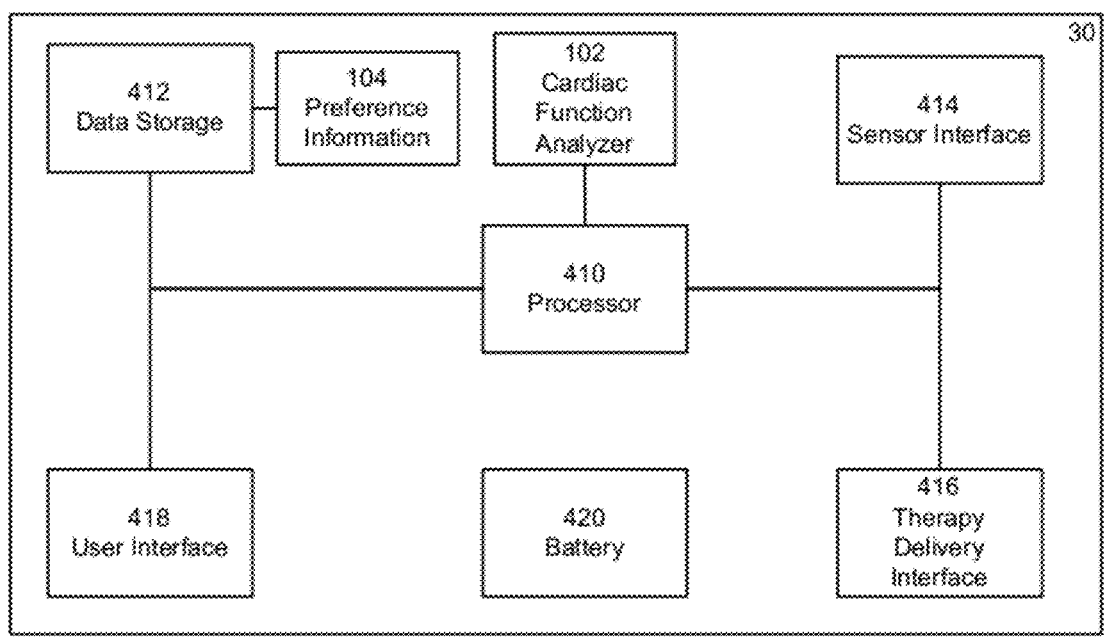
FIG. 1 is a functional schematic diagram of an exemplary control unit used to control electrode systems.

Examples disclosed herein manifest an appreciation that some patients regularly produce ECG signals that are highly idiosyncratic. In these instances, the electrical signals generated during these patient's cardiac cycles can cause conventional heart rate detection methods to detect an erroneous number of heartbeats over a given period of time. These errors are particularly problematic to a wearable medical device, such as a wearable defibrillator, because, within this context, a real-time determination of heart rate can be matter of life and death importance. For this reason, wearable medical devices that monitor heart rate tend to interpret ECG signals in a conservative light and err on the side of reporting potential arrhythmias or other cardiac malfunction to a patient, physician or others. An unfortunate side-effect of this approach is that, in some instances, patients are forced to regularly deal with falsely indicated cardiac malfunction.

The conventional heart rate detection methods mentioned above include derivative-based QRS detectors that detect heartbeats by identifying QRS complexes, to which are representative of ventricular depolarization, within an ECG signal. Conventional derivative-based QRS detectors identify QRS complexes by comparing a slope of the ECG signal to established thresholds. For example, a conventional derivative-based QRS detector may compare a magnitude of the slope of the R wave portion of the QRS complex to a threshold, and if the magnitude exceeds the threshold, the QRS detector may indicate the occurrence of a heartbeat. Typically, such derivative-based QRS detectors are configured (via hardware or software) to the morphology of the heart, and the patient.

For instance, to prevent over counting, the QRS detector may be configured to detect an occurrence of a QRS complex only after a minimum amount of time has transpired after a prior QRS complex. In some examples this minimum amount of time, which is referred to herein as the "refractory period" or the "programmed refractory period," is typically configured to be about 200 milliseconds. Moreover, the QRS detector may also be configured to use an adaptive threshold that is based upon prior samples of the patient's ECG signal, to account for variations from one patient to another, or to changes in the patient's medical condition. Upon identifying a QRS complex in this manner, conventional derivative-based QRS detectors indicate the occurrence of a heartbeat.

Given their reliance on slope, conventional derivative-based QRS detectors may double count heartbeats where a patient's normal rhythm presents an elongated QRS complex or an abnormally sharp T wave. For example, if the QRS complex generated by the patient's normal rhythm has a duration that exceeds the configured refractory period of the QRS detector, the QRS detector may detect a heartbeat at the beginning of the QRS complex and, after the refractory period has expired, detect another heartbeat near the end of the QRS complex. In another example, if the amplitude of the ECG signal is small, the adaptive thresholds used by the QRS detector may adjust to low values. In this situation, even a moderate spike in one of the other waves, such as the T wave, that occurs after expiration of the refractory period may result in a slope steep enough to cause the QRS detector to indicate the occurrence of a false heartbeat.

To address these difficulties, some exemplary wearable medical devices to disclosed herein process ECG signals from multiple channels according to a set of preference information that is tailored to fit the characteristics of the patient wearing the wearable medical device. The set of preference information may include, among other information, information indicating preferred channels and rate detection methods for the patient. For instance, in at least one example, a wearable medical device processes ECG signals received via two channels, namely a front to back channel and a side to side channel, using one or more QRS rate detectors, which may include, for example, one or more conventional QRS rate detectors. According to this example, the wearable medical device resolves conflicts between these two channels in favor of a previously identified, preferred channel. Further, in some examples, the set of preference information is automatically configured by the wearable medical device and continuously adjusted during its operation. For example, the set of preference information may be adjusted based on the current health of the patient, the activity of the patient, and the present locations of the electrodes relative to the patient's body.

The examples of the processes and apparatuses described herein are not limited in application to the details of construction and the arrangement of components set forth in the following description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, acts, elements and features discussed in connection with any one or more examples are not intended to be excluded from a similar role in any other examples.

Also, the phraseology and terminology used herein is for the purpose of description and should not be regarded as limiting. Any references to examples or elements or acts of the systems and methods herein referred to in the singular may also embrace examples including a plurality of these elements, and any references in plural to any example or element or act herein may also embrace examples including only a single element. References in the singular or plural form are not intended to limit the presently disclosed systems or methods, their components, acts, or elements. to The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Electrode System

Co-pending application Ser. No. 13/109,382, entitled WEARABLE AMBULATORY MEDICAL DEVICE WITH MULTIPLE SENSING ELECTRODES, filed May 17, 2011 (hereinafter the "'382 application"), which is incorporated by reference herein in its entirety, describes an apparatus and method for processing ECG signals using one or more channels. With reference to FIGS. 1A and 1B, the '382 application discloses an electrode system 100 that incorporates a control unit 30. As described with reference to FIG. 4 in the '382 application, at least one example of the control unit 30 includes a processor 410, data storage 412, a sensor interface 414, a therapy delivery interface 416, a user interface 418 and a battery 420.

Some of the examples disclosed herein for processing ECG signals according to a set of preferences are implemented using the electrode system 100 disclosed in the '382 application. FIG. 1 illustrates the control unit 30 of one such example. As shown in FIG. 1, the control unit 30 includes two additional components: a cardiac function analyzer 102 and preference information 104.

The cardiac function analyzer 102 is configured to analyze a portion of the ECG signal to configure preference information, such as the preference information 104, and to determine cardiac functions of the patient using the preference information. The cardiac function analyzer 102 may be implemented using hardware or a combination of hardware and software. For instance, in one example, the cardiac function analyzer 102 is implemented as a software component that is stored within the data storage 412 and executed by the processor 410. In this example, the instructions included in the cardiac function analyzer 102 program the processor 410 to configure preference information and determine the heart rate of the patient using to the preference information. In other examples, the cardiac function analyzer 102 may be an application-specific integrated circuit (ASIC) that is coupled to the sensor interface 414 and tailored to determine the heart rate of the patient. Thus, examples of the cardiac function analyzer 102 are not limited to a particular hardware or software implementation. In addition, particular examples of the processes that the cardiac function analyzer 102 is configured to perform are discussed further below with reference to FIGS. 2-6.

The preference information 104 includes data that describes parameters used by the cardiac function analyzer 102 during its analysis of ECG signals. More particularly, according to the illustrated example, the preference information 104 identifies one or more channels from which the cardiac function analyzer 102 receives ECG signals. In this example, the preference information 104 also includes information that ranks each channel relative to the other identified channels. As is discussed further below, the cardiac function analyzer 102 uses this ranking information to resolve conflicts generated from the interpretation of two or more ECG signals received via the identified channels.

In some examples, the preference information 104 also includes information indicating one or more preferred rate detectors for each channel. In these examples, the cardiac function analyzer 102 uses the preferred rate detectors of each channel to interpret the ECG signal received from each channel. In other examples, the preference information 104 includes an association that groups channel and rate detector preference information into individual profiles. In these examples, the preference information 104 also includes data that indicates an active profile that is used by the cardiac function analyzer 102 to analyze ECG signals. These examples provide the added advantage of easily configuring channel and rate detector information preferences simply by changing the indicator of the active profile from the active profile to another profile.

The preference information 104 may be stored in any logical construction capable of storing information on a computer readable medium including, among other structures, flat files, indexed files, hierarchical databases, relational databases or object oriented databases. In addition, various examples organize the preference to information 104 into particularized and, in some cases, unique structures to perform the functions disclosed herein. In these examples, the data structures are sized and arranged to store values for particular types of data.

In some examples, the components disclosed herein, such as the cardiac function analyzer 102, may read parameters that affect the functions performed by the components. These parameters may be physically stored in any form of suitable memory including volatile memory, such as RAM, or nonvolatile memory, such as a magnetic hard drive. In addition, the parameters may be logically stored in a propriety data structure, such as a database or file defined by a user mode application, or in a commonly shared data structure, such as an application registry that is defined by an operating system. In addition, some examples provide for both system and user interfaces, as may be implemented using the user interface 418, that allow external entities to modify the parameters and thereby configure the behavior of the components.

Preferential ECG Signal Processing

Figure 2:
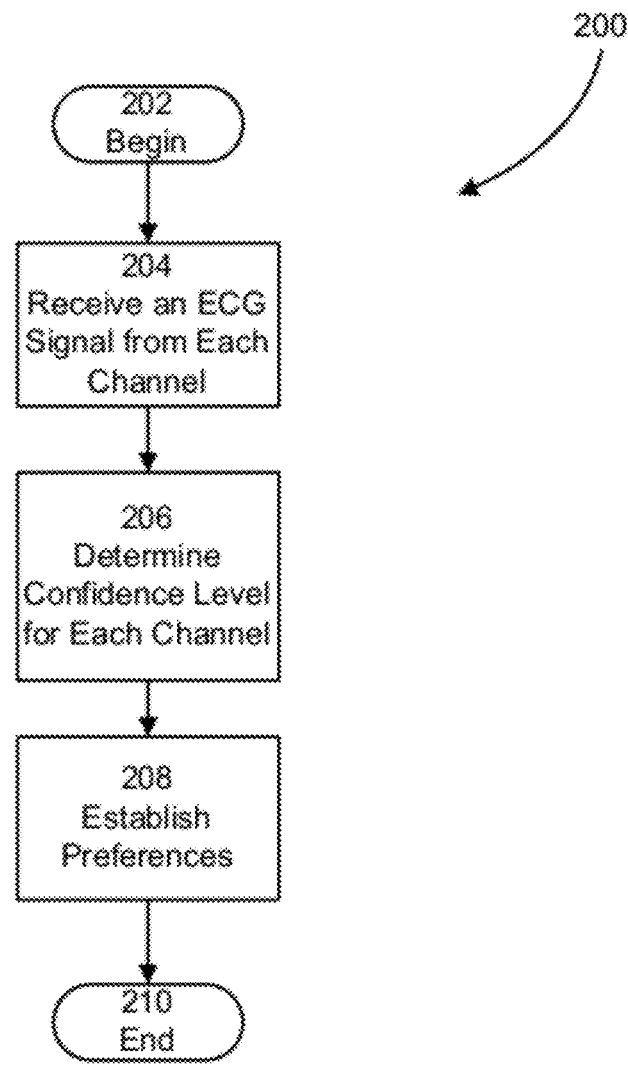
FIG. 2 is a flow chart of an exemplary process for configuring ECG signal processing preferences.

FIG. 2 illustrates a process 200 for configuring the preference information 104 according to one example. As shown, the process 200 includes acts of receiving an ECG signal from each channel, determining a confidence level for each channel and establishing preferences. The process 200 begins at 202.

In act 204, an electrode system, such as the electrode system 100 discussed above, receives one or more ECG signals via one or more channels. According to one example, the electrode system receives ECG signals from a front-to-back channel and from a side-to-side channel. The front-to-back channel includes an electrode positioned on the chest of the patient and another electrode positioned on the back of the patient. The side-to-side channel includes an electrode positioned on the left side of the chest and another electrode positioned on the right side of the patient. Other examples may employ additional, or fewer, electrodes or electrodes located in other positions on the patient's body. In addition, act 204 may include a variety of acts designed to render an accurate interpretation of the ECG signal. For instance, in one example, a control unit, such as the control unit 30 discussed above with reference to to FIG. 1, filters or otherwise manipulates the ECG signal to remove or lower the effect of noise generated by sources other than the patient's heart, such as other muscle movement or electrical disturbances near the patient.

In act 206, the filtered ECG signals are analyzed to determine a confidence level for the interpretation of each filtered ECG signal. According to the illustrated example, the filtered ECG signal of each channel is compared to benchmark information to determine a level of confidence that interpretations of the filtered ECG signal are accurate. As discussed further below, this benchmark information may include benchmark ECG signals and benchmark values that characterize attributes of a normal cardiac cycle.

Figure 3:
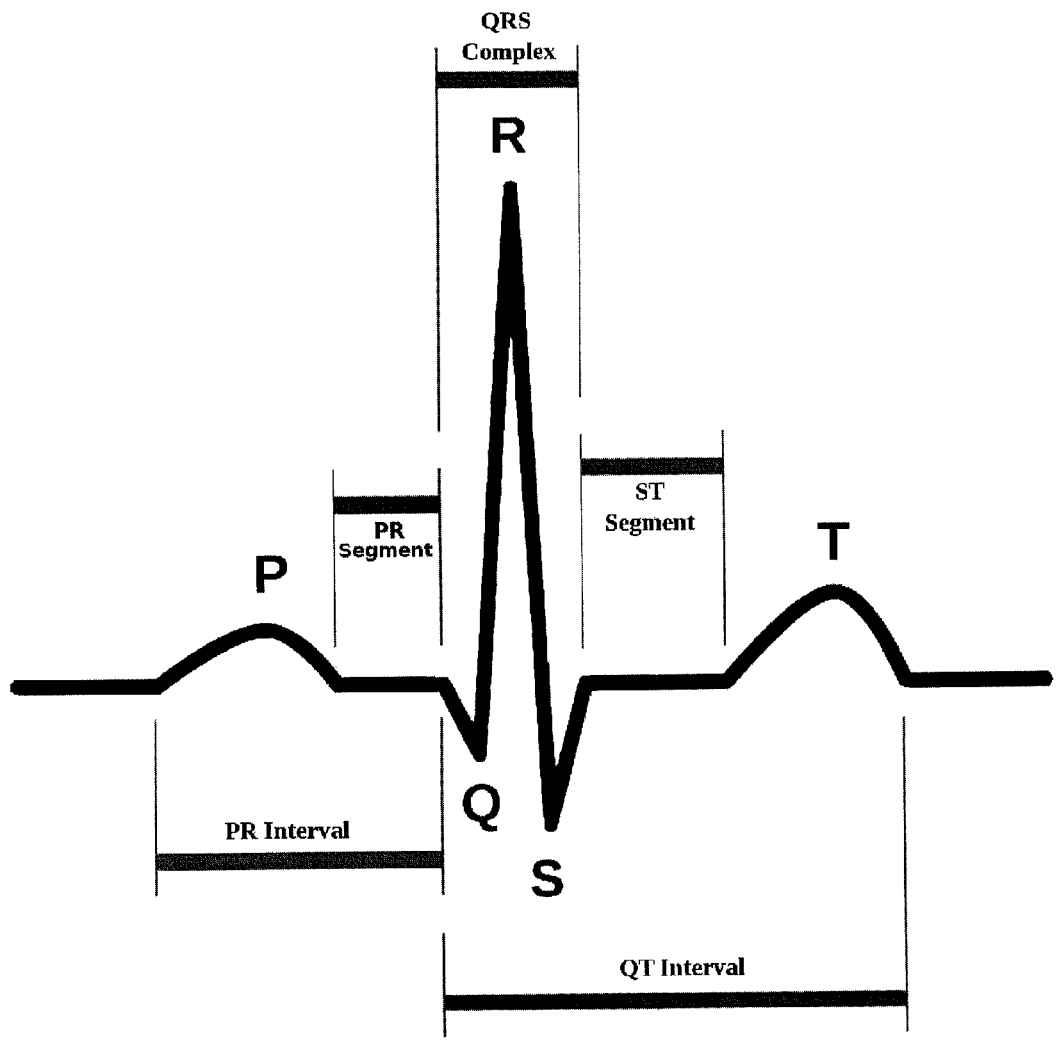
FIG. 3 is a schematic diagram of an ECG signal produced by a normal cardiac cycle.

The source of the benchmark information varies from example to example. For instance, according to one example, a standardized representation of a normal sinus rhythm, such as the ECG signal illustrated in FIG. 3, is utilized as a benchmark ECG signal. In other examples, the benchmark ECG signal includes idiosyncratic characteristics of a particular patient's normal rhythm. In these examples, the benchmark ECG signal may be received by the control unit via one or more designated channels. For instance, in one of these examples, the control unit records a benchmark ECG signal when the electrode system is initially prescribed and fitted to a patient. In addition, according to these examples, the benchmark ECG signal may adapt over time. For instance, the cardiac function analyzer 102 may adjust the benchmark ECG signal to match a composite ECG signal made up of filtered ECG signals falling within a moving window of a predefined duration. Alternatively, the benchmark ECG signal may be replaced by a newly received ECG signal with desirable characteristics such as higher amplitudes, less noise or that more closely match the normal rhythm of the patient.

Like the source of the benchmark ECG signal, the comparison operation used within the act 206 to determine the quality of interpretations of the filtered ECG signals varies between examples. In some examples, the morphology of the filtered ECG signal is compared to the morphology of the benchmark ECG signal. In these examples, the level of confidence associated with the channel that received the filtered ECG signal is directly related to the fit of the filtered ECG signal to the benchmark to ECG signal. More particularly, according to one example, a full cardiac cycle that includes P, Q, R, S and T waves is interpreted from the filtered signal. In this example, a deviation from the interpreted benchmark wave sequence of P, Q, R, S and T waves, such as one or more repeated R waves, indicates a potential double counting of a heartbeat and results in a decreased level of confidence associated with the channel. In some examples, this comparison operation is conducted by a user, such as a physician, through visual inspection.

In another example, the heart rate detected by each combination of channel and heart rate detection method is compared to the actual heart rate as determined by a user, such as a physician. In this example, the heart rate detection methods used may include derivative-based QRS detectors, spectrum analyzers or axis analyzers, as described in commonly owned U.S. Pat. No. 5,944,669 (hereinafter referred to as the "'669 patent"), which is incorporated herein by reference in its entirety. In this example, the level of confidence associated with the channel receiving the filtered ECG signal is inversely related to any difference between the heart rate detected and the actual heart rate. In addition, a level of confidence for each combination of channel and heart rate detection method may be established using this example.

In other examples, the refractory period is automatically configured to more closely fit the duration of detected QRS complexes. According to these examples, a valid QRS complex is identified by matching the morphology of the benchmark ECG signal to the morphology of the filtered ECG signal. In these examples, the refractory period is adjusted (in most cases lengthened) to encompass the duration of the valid QRS complex while the morphology of the benchmark ECG signal continues to match the morphology of the filtered ECG signal. In at least one example, an axis analyzer, such as the axis analyzer described in the '669 patent, identifies the valid QRS complex and monitors the filtered ECG signal to ensure that a match between the filtered ECG signal and the benchmark ECG is maintained. Channels with refractory periods adjusted in this manner are associated with a high level of confidence.

In act 208, preferences are established for determining the cardiac function of a given patient. In one example, preference information, such as preference information 104, is stored within the data storage 412. This preference information includes a ranking of channels based on the results of the comparison performed in act 206 with channels having a higher level of confidence being ranked above channels with a lower level of confidence. In another example, the preference information also ranks heart rate detection methods by channel, with heart rate detection methods having a higher level of confidence being ranked above heart rate detection methods having a lower level of confidence. In other examples, the ranking information may include the strength of the fit detected between the filtered ECG signal and the benchmark ECG signal or the output of the axis analyzer. In some of these examples, the strength of the fit reflects any differences in timing between interpreted ECG signal characteristics, such as QRS complexes, and interpreted benchmark ECG signal characteristics. According to a variety of examples, act 208 can be repeated at periodic intervals or as requested by a user, such as a patient or a physician. The process 200 ends at 210.

Processes in accord with the process 200 configure an electrode system, such as the electrode system 100 discussed above, to include a set of preferences for processing ECG signals. According to some examples, the process 200 is conducted by an electrode system, such as the electrode system 100 discussed above. In these examples, the data storage 412 includes the benchmark information and the cardiac function analyzer 102 conducts the acts included in the process 200. In other examples, some aspects of the process 200 are conducted by users. For instance, in one example, a user, such as a physician, performs the act 206 by determining the confidence level associated with each channel and heart rate detection method and if the user notices that the amplitude or signal to noise ratio of a particular channel is superior, the confidence level associated with that channel is increased. Further, in this example, the user performs the act 208 by storing the preference information in the electrode system, via a user interface, such as the user interface 418.

According to another example, the user, such as a physician, performs the act 208 by causing the preference information to be stored on the control unit of an electrode system via a network interface. In this example, a processor included in the control unit of the electrode system, such as the processor 410 of the control unit 30, to is coupled to a network interface such as the network interface 206 described in co-pending application Ser. No. 12/833,096, entitled SYSTEM AND METHOD FOR CONSERVING POWER IN A MEDICAL DEVICE, filed Jul. 9, 2010, which is incorporated by reference herein in its entirety.

Figure 4:
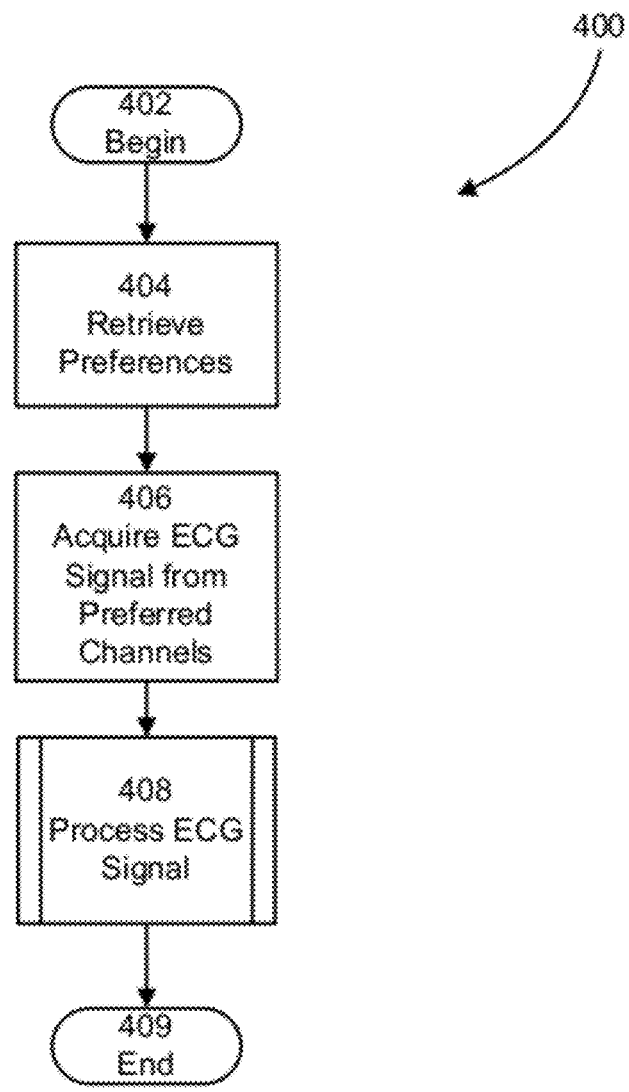
FIG. 4 is a flow chart of an exemplary process for detecting cardiac function from a portion of an ECG signal.

FIG. 4 illustrates an exemplary process 400 for interpreting ECG signals using preference information. As shown, the process 400 includes acts of retrieving preferences, acquiring ECG signals from preferred channels and processing the ECG signals according to the retrieved preferences. The process 400 begins at 402.

In act 404, the cardiac function analyzer 102, discussed above, retrieves preference information, such as preference information 104 discussed above, from data storage. According to one example, the preference information includes information ranking the channels through which ECG signals can be received and further indicating a preferred set of ranked channels. In another example, the preference information includes information ranking the heart rate detection methods available for each ranked channel and indicating a preferred set of heart rate detection methods.

In act 406, the cardiac function analyzer 102 acquires ECG signals from each of the preferred set of ranked channels. The electrode system may perform a variety of acts designed to render an accurate interpretation of the ECG signal. For instance, in one example, a control unit, such as the control unit 30 discussed above with reference to FIG. 1, filters or otherwise manipulates the ECG signal to remove or lower the effect of noise generated by sources other than the patient's heart, such as other muscle movement or electrical disturbances near the patient.

Figure 5:
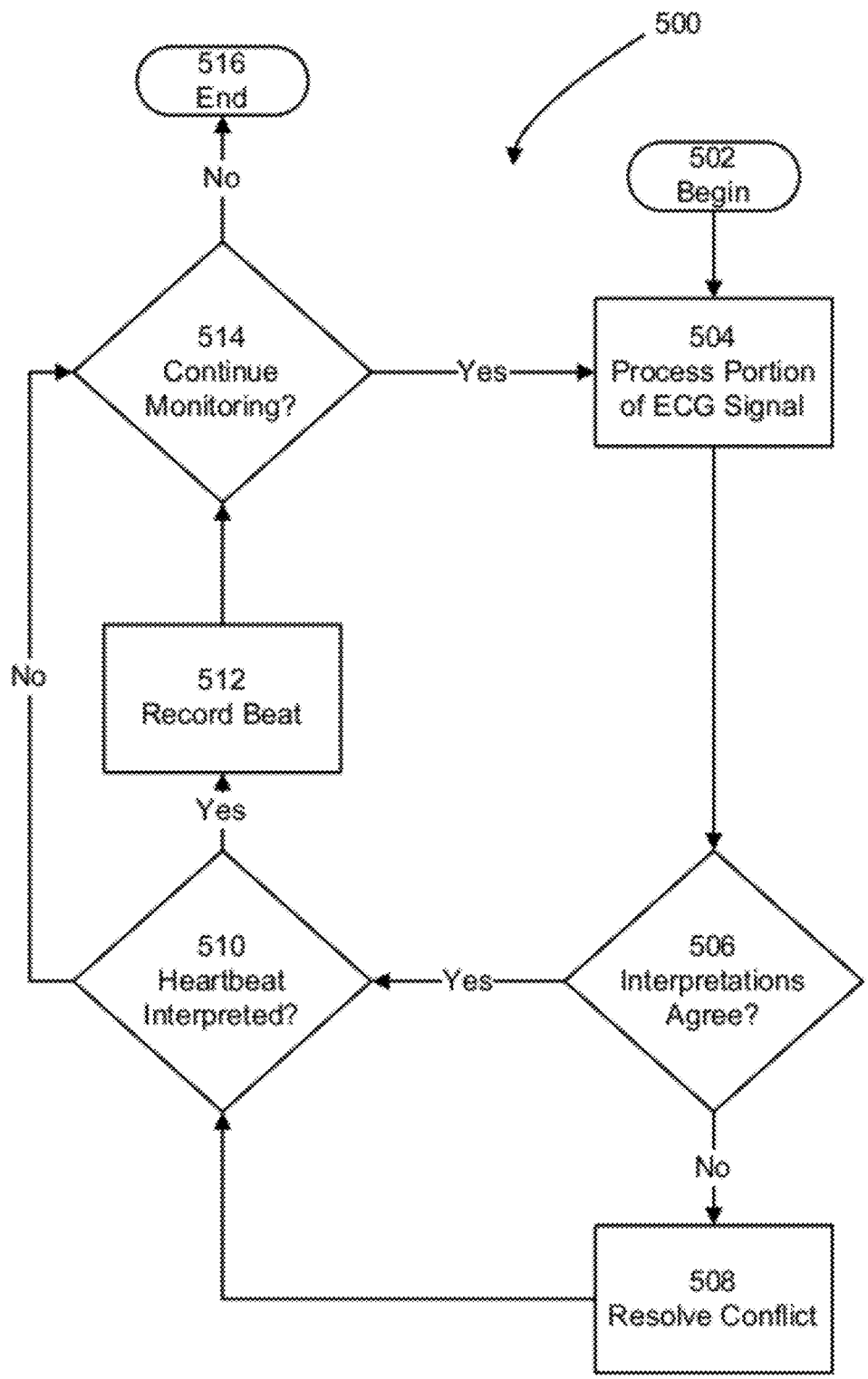
FIG. 5 is a flow chart of an exemplary process for interpreting ECG signals according to a set of ECG signal processing preferences.

In act 408, the cardiac function analyzer 102 processes the ECG signals to determine a heart rate for the patient. FIG. 5 illustrates an exemplary process 500 in accord with act 408. As shown, the process 500 begins at 502.

In act 504, the cardiac function analyzer 102 processes a portion of the filtered ECG signal received by each preferred channel using one or more of the heart rate detection methods discussed above with reference to the process 200. For instance, the cardiac function analyzer 102 may utilize conventional derivative-based QRS to detectors, axis detectors or others. According to a particular example discussed further below, when the cardiac cycle appears to be in a normal sinus rhythm, the cardiac function analyzer 102 determines a heart rate using both a QRS detector and an axis detector. In this example, the axis detector indicates the occurrence of a heartbeat when a peak in the magnitude indicated by the axis detector corresponds to a zero phase crossing. In another example, the axis detector may concurrently compare the quality of the fit of multiple ECG signals coming from multiple channels to a benchmark ECG and may use the heart rate determined in this manner provided that the quality of the fit between the benchmark ECG signal and the multiple ECG signals meets a predetermined value. In still another example, a single channel fit is performed using the axis detector. In these examples that utilize an axis detector, the quality of the fit is determined by summing errors calculated between samples of the benchmark ECG signal and one or more ECG signals over an identified period.

In act 506, if the results of these methods agree (for example, if each method detects a single heartbeat from the portion of the interpreted ECG signal) then the cardiac function analyzer 102 proceeds to act 510. Otherwise, the cardiac function analyzer 102 proceeds to act 508. In act 508, the cardiac function analyzer 102 resolves conflicts between channels and heart rate detection methods. The particular conflict resolution procedure employed varies from example to example and examples are not limited to a particular approach to resolving conflicting results between channels or combinations of channels and heart rate detection methods. For instance, according to one example, the cardiac function analyzer 102 resolves conflicts that involve multiple channels in favor of the highest ranking preferred channel. In another example, the cardiac function analyzer 102 resolves conflicts that involve multiple channels and heart rate detectors in favor of the result indicated by a majority of the channel and heart rate detector combinations. Continuing with the particular example discussed above involving the QRS and axis detectors, conflicts between QRS detector results on separate channels are resolved in favor of the channel with a result that agrees with the axis detector result.

In act 510, if the all of the interpretations, or the favored interpretations, of the ECG signals indicate that a heartbeat has occurred, the cardiac function analyzer 102 to records the occurrence of a heartbeat in act 512. Otherwise, the cardiac function analyzer 102 determines if an interruption in monitoring is about to commence, such as an interruption caused by shutdown of the electrode system, in act 514. If so, the cardiac function analyzer ends the process 500 at 516. Otherwise, the cardiac function analyzer 102 returns to act 504 and the process 500 continues.

Examples in accord with process 500 enable an electrode system to more accurately track patient heart rate. More accurate heart rate tracking results in several benefits. These benefits include more accurate patient historical information and generation of fewer falsely indicated arrhythmias. Fewer false arrhythmias, in turn, may result in avoidance of unnecessary alarms and delivery of therapy to a patient, thereby increasing the runtime between charges of the electrode system and avoiding unnecessary patient discomfort.

Each of the processes disclosed herein depicts one particular sequence of acts in a particular example. The acts included in each of these processes may be performed by, or using, an electrode system specially configured as discussed herein. Although described herein in association with an electrode system of a wearable defibrillator such as the LIFEVEST Cardioverter defibrillator, embodiments disclosed herein may be used with any electrode system, including conventional stick-on adhesive electrodes, dry capacitive ECG electrodes, radio transparent electrodes, etc. Some acts are optional and, as such, may be omitted in accord with one or more examples. Additionally, the order of acts can be altered, or other acts can be added, without departing from the scope of the systems and methods discussed herein. In addition, as discussed above, in at least one example, the acts are performed on a particular, specially configured machine, namely an electrode system configured according to the examples disclosed herein.

Usage Scenario

Figure 6:
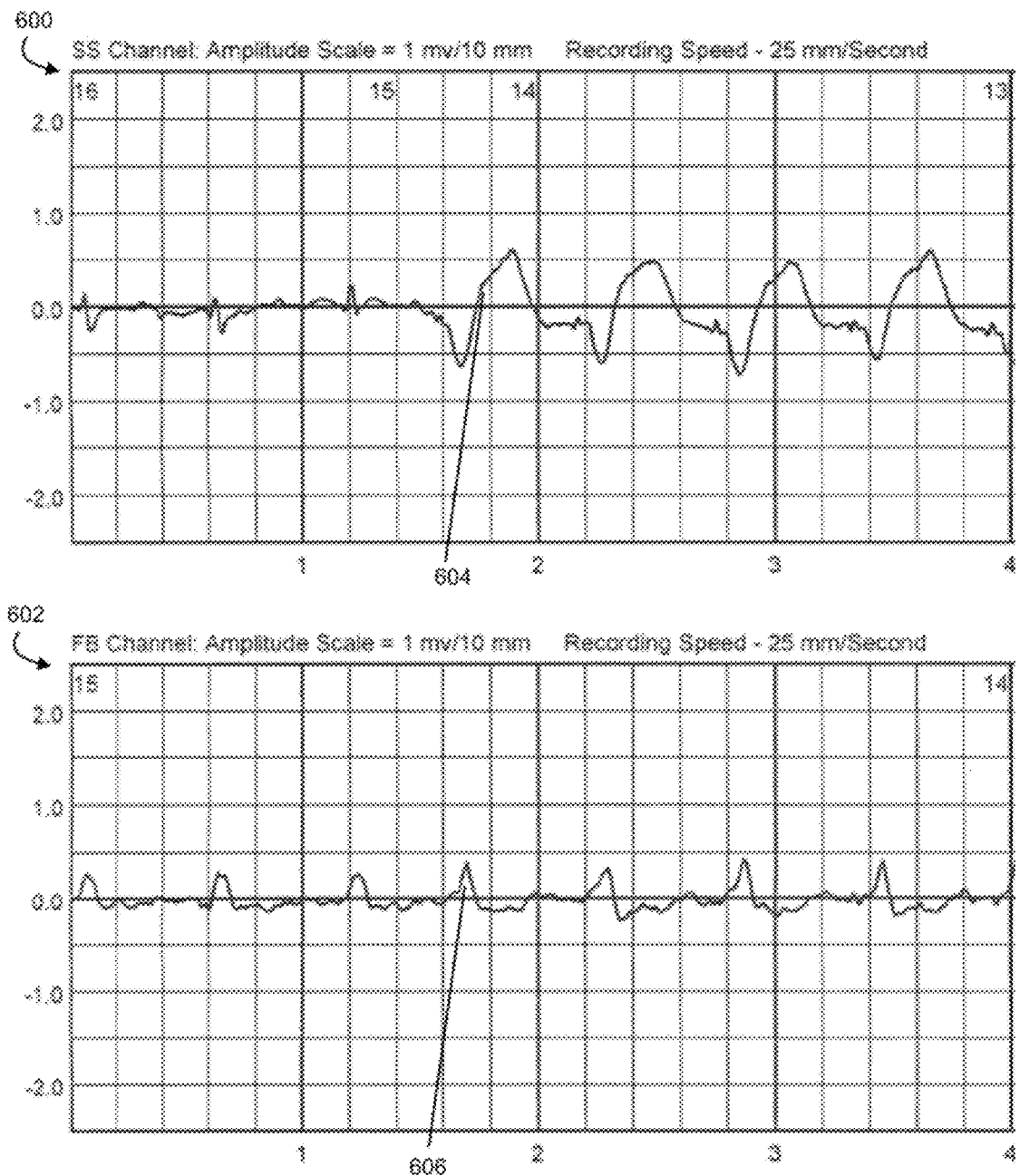
FIG. 6 is an exemplary ECG signal produced by an idiosyncratic cardiac cycle.

FIG. 6 illustrates two exemplary idiosyncratic ECG signals 600 and 602 received by an exemplary electrode system. As shown, the ECG signal 600 was acquired via a side-to-side (SS) channel and includes QRS complex 604. The ECG signal 602 was acquired via a front-to-back (FB) channel and includes QRS complex to 606. As illustrated, the ECG signal 600 may be double counted by conventional derivative-based QRS complex detectors because the QRS complexes presented within the ECG signal 600, such as the portion of the ECG signal indicated by reference number 604, are elongated and exceed the default configuration of the refractory period. Thus, conventional derivative-based QRS complex detectors may detect a first QRS complex at the onset of the QRS complex 604 and detect a second QRS complex near the end of the QRS complex 604 after the refractory period has expired.

According to one example, a user, such as a physician, may perform act 206 of process 200 and thereby determine that the SS channel is susceptible to double counting by comparing the morphology of the ECG signal acquired via the SS channel to an ECG signal representative to a normal sinus rhythm. Further, the user may perform act 208 by configuring preference information to rank the FB channel higher than the SS channel. After receiving this preference information and during the execution of process 400, the exemplary electrode system favors the FB channel over the SS channel if the two channels yield differing heart rates. This approach results in a decreased likelihood of heartbeat double counting because the QRS complexes displayed within the FB channel do not extend beyond the programmed refractory period and are, therefore, less likely to be double counted.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the scope of the invention. Accordingly, the foregoing description and drawings are by way of example only.

What is claimed is:

1. An ambulatory medical device, comprising:
a plurality of electrodes disposed at spaced apart positions about a patient's body; and
a control unit including:
a sensor interface coupled to the plurality of electrodes and configured to receive a first ECG signal from a first pairing of the plurality of electrodes and to receive a second ECG signal from a second pairing of the plurality of electrodes;
a memory storing a configurable parameter indicating a preferred pairing, the preferred pairing being either the first pairing or the second pairing; and
a processor coupled to the sensor interface and the memory, the processor comprising a cardiac function analyzer to process the first ECG signal to determine a first ECG signal interpretation of a physical condition of the patient, to process the second ECG signal to determine a second ECG signal interpretation of the physical condition of the patient, to detect a conflict between ECG signal interpretations wherein the conflict comprises a difference in the physical condition of the patient under the first ECG signal interpretation and the second ECG signal interpretation, and to resolve the conflict by retrieving the preferred pairing from the configurable parameter stored in the memory and resolving the conflict in favor of the preferred pairing.

2. The ambulatory medical device of claim 1, further comprising a garment that is configured to be worn about the patient's body, wherein the plurality of electrodes is integrated into the garment.

3. The ambulatory medical device of claim 1, wherein the plurality of electrodes includes adhesive electrodes.

4. The ambulatory medical device of claim 1, wherein the first ECG signal interpretation and the second ECG signal interpretation indicate heartbeats.

5. The ambulatory medical device of claim 4, wherein the configurable parameter includes information indicating a second heart rate detection method preferred for the second paring, and wherein the processor is further configured to:
interpret the first ECG signal using the first heart rate detection method; and
interpret the second ECG signal using the second heart rate detection method.

6. The ambulatory medical device of claim 1, wherein the processor is further configured to:
determine a first confidence level for the first pairing;
determine a second confidence level for the second pairing;
determine the preferred pairing with reference to the first confidence level and the second confidence level; and
store the information indicating the preferred pairing in the memory.

7. The ambulatory medical device of claim 6, wherein the processor is configured to determine the first confidence level by comparing the first ECG signal to benchmark information.

8. The ambulatory medical device of claim 7, wherein the benchmark information reflects a normal rhythm of the patient.

9. The ambulatory medical device of claim 7, wherein the processor is configured to compare the first ECG signal to the benchmark information by comparing a morphology of the first ECG signal to a morphology indicated within the benchmark information.

10. The ambulatory medical device of claim 1, wherein the ambulatory medical device includes a treatment device.

11. The ambulatory medical device of claim 1, wherein the control unit further includes a user interface configured to receive input from a user to configure the configurable parameter.

12. The ambulatory medical device of claim 1, wherein the physical condition is a detected heart rate of the patient.

13. A method of monitoring ECG signals using an ambulatory medical device including a memory and a plurality of electrodes, the method comprising:
storing, in the memory, a configurable parameter indicating a preferred pairing, the preferred pairing being either a first pairing of the plurality of electrodes or a second pairing of the plurality of electrodes;
receiving, by the ambulatory medical device, a first ECG signal from the first pairing of the plurality of electrodes;
receiving a second ECG signal from the second pairing of the plurality of electrodes;
processing the first ECG signal to determine a first ECG signal interpretation of a physical condition of the patient;
processing the second ECG signal to determine a second ECG signal interpretation of the physical condition of the patient;
detecting a conflict between ECG signal interpretations wherein the conflict comprises a difference in the physical condition of the patient under the first ECG signal interpretation and the second ECG signal interpretation; and
resolving the conflict by retrieving the preferred pairing from the configurable parameter stored in the memory and resolving the conflict in favor of the preferred pairing.

14. The method of claim 13, wherein processing the first ECG signal to determine the first ECG signal interpretation includes processing the first ECG signal to detect a heartbeat of the patient and wherein processing the second ECG signal to determined the second ECG signal interpretation includes processing the second ECG signal to detect the heartbeat of the patient.

15. The method of claim 13, further comprising:
interpreting the first ECG signal using a first heart rate detection method; and
interpreting the second ECG signal using a second heart rate detection method.

16. The method of claim 13, further comprising:
determining a first confidence level for the first pairing;
determining a second confidence level for the second pairing; and
determining the preferred pairing with reference to the first confidence level and the second confidence level.

17. The method of claim 16, wherein determining the first confidence level includes comparing the first ECG signal to benchmark information.

18. The method of claim 17, wherein comparing the first ECG signal to the benchmark information includes comparing the first ECG signal to benchmark information that reflects a normal rhythm of the patient.

19. The method of claim 17, wherein comparing the first ECG signal to the benchmark information includes comparing a morphology of the first ECG signal to a morphology indicated within the benchmark information.

20. A non-transitory computer readable medium having stored thereon sequences of instruction for monitoring ECG signals including instructions that instruct at least one processor to:
store, in a memory, a configurable parameter indicating a preferred pairing, the preferred pairing being either a first pairing of a plurality of electrodes or a second pairing of a plurality of electrodes;
receive a first ECG signal from the first pairing of the plurality of electrodes;
receive a second ECG signal from the second pairing of the plurality of electrodes;
process the first ECG signal to determine a first ECG signal interpretation of a physical condition of the patient;
process the second ECG signal to determine a second ECG signal interpretation of the physical condition of the patient;
detect a conflict between ECG signal interpretations wherein the conflict comprises a difference in the physical condition of the patient under the first ECG signal interpretation and the second ECG signal interpretation; and
resolve the conflict by retrieving the preferred pairing stored in the configurable parameter in the memory and resolve the conflict in favor of the preferred pairing.

21. The computer readable medium of claim 20, wherein the instructions further instruct the at least one processor to:
determine a first confidence level for the first pairing;
determine a second confidence level for the second pairing; and
determine the preferred pairing with reference to the first confidence level and the second confidence level.

22. The computer readable medium of claim 21, wherein the instructions that instruct the at least one processor to determine the first confidence level include instructions that instruct the at least one processor to compare the first ECG signal to benchmark information.

23. The computer readable medium of claim 22, wherein the instructions that instruct the at least one processor to compare the first ECG signal to the benchmark information include instructions that instruct the at least one processor to compare a morphology of the first ECG signal to a morphology indicated within the benchmark information.

* * * * *

UNITED STATES PATENT AND TRADEMARK OFFICE
CERTIFICATE OF CORRECTION

PATENT NO. : 8,897,860 B2  
APPLICATION NO. : 13/428329  
DATED : November 25, 2014  
INVENTOR(S) : Shane S. Volpe et al.

Page 1 of 1

It is certified that error appears in the above-identified patent and that said Letters Patent is hereby corrected as shown below:

In the Specification:

Column 3, Line 6, delete "to".

Column 3, Line 46, delete "to".

Column 4, Line 21, delete "In the to drawings" and insert -- In the drawings --.

Column 6, Line 8, delete "to".

Column 7, Line 23, delete "to".

Column 7, Line 63, delete "to to" and insert -- to --.

Column 8, Line 38, delete "benchmark to" and insert -- benchmark --.

Column 10, Line 30, delete "to".

Column 11, Line 6, delete "to".

Column 11, Line 47, delete "to".

Signed and Sealed this  
Fourth Day of August, 2015

Michelle K. Lee  
*Director of the United States Patent and Trademark Office*